United States Patent [19]

Mazur et al.

[11] Patent Number: 5,104,797
[45] Date of Patent: Apr. 14, 1992

[54] PROCESS FOR PREPARING 5-C-HYDROXYMETHYL ALDOHEXOSE-BASED COMPOUNDS

[75] Inventors: Adam W. Mazur, Cincinnati; George D. Hiler, II, Harrison; Gordon K. Stipp, Cincinnati; Bernard W. Kluesener, Harrison, all of Ohio

[73] Assignee: The Procter & Gamble Company, Cincinnati, Ohio

[21] Appl. No.: 337,725

[22] Filed: Apr. 17, 1989

Related U.S. Application Data

[63] Continuation-in-part of Ser. No. 190,485, May 5, 1988, abandoned.

[51] Int. Cl.$^5$ .................. C12P 19/02; C12P 19/04; C12N 9/04; C07N 1/00
[52] U.S. Cl. .................. 435/105; 435/101; 435/190; 536/1.1; 536/4.1
[58] Field of Search .................. 435/105, 190, 101; 536/1.1

[56] References Cited

U.S. PATENT DOCUMENTS

| | | | |
|---|---|---|---|
| 2,876,105 | 3/1959 | Jucaitis et al. | 99/141 |
| 3,600,186 | 8/1971 | Mattson et al. | 99/1 |
| 3,704,138 | 11/1972 | LaVia et al. | 99/141 |
| 3,954,976 | 5/1976 | Mattson et al. | 424/180 |
| 3,963,699 | 6/1976 | Rizzi et al. | 260/234 |
| 4,005,195 | 1/1977 | Jandacek | 424/180 |
| 4,005,196 | 1/1977 | Jandacek | 424/180 |
| 4,207,413 | 6/1980 | Szarek et al. | 536/1 |
| 4,262,032 | 4/1981 | Levin | 426/658 |
| 4,382,924 | 5/1983 | Berling et al. | 424/180 |
| 4,459,316 | 7/1984 | Bakal | 426/658 |

OTHER PUBLICATIONS

"The Sweetener Report, 1982–1987", Food Engineering, 54, No. 7, 75–83, 85, (1982).
Witzak and Whistler, Carbohydrate Research, 169, 252–257, (1987).
Kirk-Othmer, *Encyclopedia of Chemical Technology*, 3rd ed., 21, p. 939, (1978).
Rothschild, Food Chemical News Guide, p. 255, (1987), p. 430, (1982), p. 495, (1986).
CRC, vol. 11, No. 4, pp. 401–413, (1979).
Mardufu et al., *Can. J. Chem.*, 50,768 (1961).
Whyte et al., *Carbohds Res.*, 57,273 (1977).
Jacket et al., *Carbohds Res.*, 49,335, (1976).
Root et al., J. Am. Chem. Soc., 107,2997–2999, (1985).
Yalpani and Hall, *J. Poly. Sci.*, 20, 3399–3420, (1982).
Schaffer, *J. Am. Chem. Soc.*, 81, 5452–5454, (1959).
Leland et al., Carbohyds Res., 38, pp. C9–C11, (1974).
Youssefyeh et al., J. Org. Chem., 44 (8), 1301–1317, (1979).
Dziezek, *Food Technology*, 111–130, (1986).
Paul & Palmer, Food Theory and Application, p. 47, (1972).

*Primary Examiner*—Johnnie R. Brown
*Assistant Examiner*—Pamela S. Webber
*Attorney, Agent, or Firm*—Rose Ann Dabek; Jerry J. Yetter; Richard C. Witte

[57] ABSTRACT

Processes of the present invention provide economical methods for preparing derivatives 5-C-hydroxymethyl-D-aldohexose and their bicyclic anhydro tautomeric forms. The 5-C-hydroxymethylation process comprises an enzymic oxidation reaction followed by a condensation reaction with formaldehyde.

37 Claims, No Drawings

PROCESS FOR PREPARING 5-C-HYDROXYMETHYL ALDOHEXOSE-BASED COMPOUNDS

This application is a continuation-in-part of Ser. No. 07/190,485, filed May 5, 1988, now abandoned.

TECHNICAL FIELD

This invention relates to an economical method for preparing 5-C-hydroxymethyl-D-aldohexose-based compounds. More specifically, it relates to the 5-C-hydroxymethylation of D-aldohexose compounds, D-aldohexosyl functional groups, and D-aldohexoside functional groups. The 5-C-hydroxymethylation process comprises an enzymatic oxidation reaction followed by a condensation reaction with formaldehyde. These process steps may be followed by a hydrolysis step which produces the bicyclic anhydro tautomeric form of the 5-C-hydroxymethyl-D-aldohexose based monosaccharides.

BACKGROUND OF THE INVENTION

The ready availability of a variety of highly flavorful food products coupled with the relatively sendentary lifestyles of a good segment of the population has given rise to an excess accumulation of calories in many people. Estimates indicate that currently as much as 40% of the U.S. application is overweight. J. Beereboom, *CRC Critical Reviews in Food Science and Nutrition*, 11(4), pps. 401–413, May 1979. Consequently, an increasing number of consumers are practicing some form of dieting and monitoring of caloric intake. This is evidenced by the successful introductions and rapid growth of a variety of reduced calorie products, such as cake mixes, beers, wines, candies and sodas into the food market.

Two of the most significant contributors to the population's calorie intake are sucrose (i.e., common table sugar) and high fructose corn syrup. In fact, a great deal of effort has been expended in the food sciences to develop a functional reduced calorie sugar substitute.

In 1985, the Calorie Control Council's brochure *Sweet Choices* described in ideal sweetener as having the following characteristics:
same or greater sweetness as sucrose
colorless
odorless
readily soluble in water
stable
functionally similar to sucrose
economically feasible
contribute reduced or no calories to the diet
non-toxic and non-promoting of dental caries
The Council commented that up to that data a sweetener having all those characteristics did not exist.

Sugars are best known as sweeteners, however, their role as functional components in foods is equally important. Sugar influences many properties of food in addition to flavor. It alters the degree of hydration of many substances, influences the viscosity of starch pastes, the firmness of gelatin and pectin gels, and the formation and strength of gluten strands. It controls the gelatinization temperature of starch and the gelation temperatures of gluten and egg proteins. It affects the rate of spoilage due to the growth of micro-organisms. In many cases, it alters the color and texture of fruit products. It increases the moisture-retaining ability of many foods. The size of sugar crystals influences markedly the textural characteristics of candies and frostings and it enhances the body of beverages. (See Paul and Palmer, *Food Theory and Applications*, pp. 47 (1972)). All of these properties are regulated by varying the concentration of sugar in the food product. As a result, the volume fraction of sugar in foods is often very high. This is commonly referred to as sugar's bulking characteristic. One of the major problems in developing a reduced calorie sugar substitute is to provide this bulking characteristic.

Most artificial sweeteners in use today have a relative sweetness greater than sucrose; thus, relatively small quantities are required to deliver the desired sweetness. Such low volume sweeteners may be acceptable for certain applications (e.g., beverages), however, they do not provide sufficient bulk and functionality for use in solid and semi-solid foods like baked goods and frozen desserts. In fact, even high intensity sweetener-containing beverages have a detachable reduction in their body. Two avenues have been explored to overcome this bulking problem:
combinations of bulk extenders and available artificial sweeteners
modified sugars Presently-available sweeteners and sweetener/bulk extender combinations are not satisfactory due to their significant deviation from the important functional characteristics of sucrose (e.g., solubility and control of starch gelatinization), significant calorie values, and negative physiological effects.

Polydextrose, produced by Pfizer Corp., is a non-sweet, randomly bonded glucan containing small amounts of sorbitol and citric acid. It is presently the most widely used reduced calorie bulk extender in foods. As a sugar substitute it contributes 1 kcal/g, which is equivalent to about 25% of the calorie contribution of sucrose.

U.S. Pat. No. 2,876,105, Jucaitis and Biudzius, issued Mar. 3, 1959, discloses another class of carbohydrate polymers to be used as bulk extenders. Other bulk extenders include gum arabic and gum tragacanth. However, they are not desirable since they are not readily soluble, especially in cold liquids, and they have high relative viscosities and they have little control of starch gelatinization. See U.S. Pat. No. 3,704,138, LaVia, issued Nov. 28, 1972.

Arabinogalactan (Larch Gum) is a highly branched polymer of arabinose and galactose obtained from the Western Larch tree. Though it has FDA clearance for use in foods and has many suitable physical properties, such as good solubility in solutions having low viscosities, actual use has been small due to taste, functionality, heat-stability problems, and poor starch gelatinization control.

U.S. Pat. No. 4,207,413, Szarek et al., issued Jun. 10, 1980, discloses that L-sucrose ($\alpha$-L-glucopyranosyl-$\beta$-L-fructofuranoside) has identical sweetness to sucrose but is not metabolized on ingestion and is, therefore, non-caloric. The high cost of synthesizing this compound acts as a significant barrier to its development as a dietary sweetening agent. See Kirk-Othmer, *Encyclopedia of Chemical Technology*, third ed., vol. 21, pg. 939 (1978). A later patent discloses that L-monosaccharides are also edible and non-caloric (U.S. Pat. No. 4,262,032, Levin, issued Apr. 14, 1981). These L-sugars are also very costly to synthesize.

Sugar alcohols, called alditols, have also been proposed as sugar substitutes. However, only a few alditols have been approved as food additives and they have limited dietary applications due to their low laxative threshold and significant caloric value. (See, Rothschild, *Food Chemical News Guide,* mannitol, pg. 255 (1987); sorbitol, pg. 430 (1982); xylitol, pg. 495 (1986)).

In order to test structure-sweetness correlations, Witczak and Whistler, Carbohydrate Research, 169 (1987), 252-257, synthesized many compounds, including a large group of compounds including the branched-chain alditol, 2-C-(hydroxymethyl)-D-mannitol. Witczak and Whistler did not comment on the metabolizability of compound.

U.S. Pat. No. 4,459,316, Bakal, issued Jul. 10, 1984, teaches that di- and trisaccharides containing one levohexose component and at least one dextrohexose component (e.g., α-L-glucopyranosyl-β-D-fructofuranose) are non-caloric. These disaccharides are costly to synthesize due to the fact that they are prepared from a racemic mixture of D-hexoses and expensive L-hexoses.

Thus, there has not yet been developed in the art a sugar replacement component which is low in calories, inexpensive to synthesize, sweet, functional (especially as a bulking agent) and avoids negative physiological effects. It would be highly desirable to define such a compound.

It has been found (U.S. patent application, Ser. No. 190,486, filed May 5, 1988 by Mazur) that derivatives of 5-C-hydroxymethyl-D-hexose compounds can be used as replacements for sugar, especially in baked goods. These carbohydrates provide sugar-like functionality (i.e., bulk, texture and stability) with significantly reduced calories compared with sucrose. It has also been shown that saccharides containing a 5-C-hydroxymethyl-D-aldohexosyl or 5-C-hydroxymethyl-D-ketohexosyl component provide similar benefits. This also holds true for the alditols of these carbohydrates, 5-C-hydroxymethyl-D-aldohexosyl polyol derivatives, alkyl derivatives of the carbohydrates (i.e., alkyl 5-hydroxymethyl-D-aldohexoside or alkyl 5-hydroxymethyl-D-ketohexoside), and 1,6-anhydro-β-D-, and 1,6-anhydro-β-L-derivatives of the pyranose compounds (i.e., the bicyclic tautomeric forms).

Galactose oxidase has the particular characteristic of converting the C-6 hydroxy group in galactose to the corresponding aldehyde (See Mardufu et al., Can. J. Chem., 50, 768 (1971)). The reaction has been successfully applied to a number of mono- and polysaccharides (See Whyte et al., Carbohds. Res., 57, 273 (1977); Jacket et al., Carbohds. Res, 49, 335 (1976)). Root et al., J. Am. Chem. Soc., 107, 2997 (1985), have recently shown that this enzymic synthesis can be applied to polyols. Also, Yalpani and Hall, J. Poly. Sc., 20, 3399-3420 (1982), have cataloged a significant number of applications for the product of the galactose oxidase reaction (e.g., reductive amination, oxidation and reduction).

Schaffer, J. Am. Chem. Soc., 81, 5452 (1959), teaches that 4-hydroxymethyl pentose may be condensed from its corresponding aldehyde with formaldehyde in aqueous sodium hydroxide. This reaction has recently been applied to other sugars (See Carbohds. Res., 38 (1974), pp. C9-C11 and J. Org. Chem., 44 (8), 1301-1317 (1979)).

It has now been found that the 5-C-hydroxymethylation of D-aldohexose compounds, D-aldohexosyl functional groups and D-aldohexoside functional groups, can be accomplished by an enzymic conversion reaction followed by a condensation reaction with formaldehyde. This reaction provides a functional sugar replacement (i.e., a 5-C-hydroxymethyl-D-aldohexose-based compound in a very economical manner.

SUMMARY OF THE INVENTION

The process of the present invention encompasses a method of preparing derivatives 5-C-hydroxymethyl-D-aldohexose compounds which comprises the following steps. First, reacting under agitation and aeration and aqueous solution comprising from about 1% to about 50% D-aldohexose-based compound or a mixture of D-aldohexose-based and from about 1,000 to about 1,000,000 unit activity of the enzyme D-aldohexose:oxygen 6-oxidoreductase per mole of D-aldohexose-based compound at a temperature of from about 1° C. to about 50° C. Second, condensing the resulting oxidation product by reacting the solution with from about 1 to about 40 molar equivalents of formaldehyde and from about 1 to about 13 molar equivalents of a base selected from the group consisting of sodium hydroxide, calcium hydroxide, potassium hydroxide, and mixtures thereof, at a temperature of from about 15° C. to about 40° C. and at a pH of from about 12 to about 13. Finally, the aqueous 5-C-hydroxymethyl-D-aldohexose-based compound containing solution is purified.

The invention also includes a method for converting the 5-C-hydroxymethylated compounds formed above to their anhydro bicyclic form by (1) hydrolyzing the 5-C-hydroxymethylated product described above with from about 1 to about 10 molar equivalents of a mineral acid or strong organic acid selected from the group consisting of sulfuric acid, nitric acid, hydrochloric acid, perchloric acid, phosphoric acid, methanesulfonic acid, trifluoromethanesulfonic acid, or mixture thereof, at a temperature from about 20° C. to the boiling point; and (2) removing any residual acid from the reaction solution.

DETAILED DESCRIPTION OF THE INVENTION

The term "D-aldohexoses" refers to the group of sugars whose molecule contains six carbon atoms, one aldehyde group and five alcohol groups. The eight stereoisomers of the D-aldohexose series are D-allose, D-altrose, D-glucose, D-mannose, D-gulose, D-idose, D-galactose, and D-talose. These sugars exist in solution as an equlibrium mixture of several "tautomeric forms": a pyran-ring form; a furan-ring form, and a straight-chain aldehyde form. Tautomeric forms of D-glucose are:

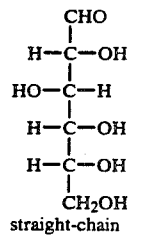
straight-chain

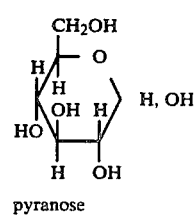
pyranose

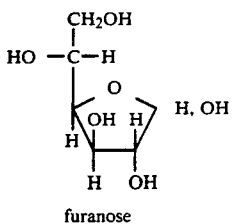

furanose

Aldohexoses may also occur in an α or β anomeric configuration, depending on the position of the C-1 hydroxyl group. Examples are:

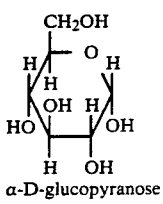

α-D-glucopyranose

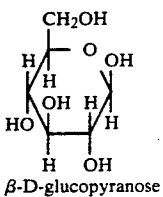

β-D-glucopyranose

The term "polyol" includes all polyhydric alcohols (i.e., those compounds of the general formula $CH_2OH(CHOH)_nCH_2OH$, where n may be form 0 to 5.) The compound containing three hydroxyl groups is glycerol, those with more than three hydroxyl groups are called sugar alcohols.

The terms "D-aldohexose-based compound", and "derivatives of D-aldohexose compounds" as used herein, refer to a compound selected from the group consisting of D-aldohexoses, D-aldohexosyl polyols; alkyl D-aldohexosides, D-hexitols; and di-, tri-, oligo- or polysaccharides comprising one or more of the above-mentioned simple sugar linkages.

The term "galactose oxidase", as used herein, refers to D-galactose:oxygen 6-oxidoreductase which is identified as E. C. 1.1.3.9 or as Chemical Abstracts Registry Number 9028-79-9.

The term "D-aldohexose:oxygen 6-oxidoreductase", as used herein, refers to enzymes which convert the C-6 hydroxy group in an aldohexose to the corresponding aldehyde:

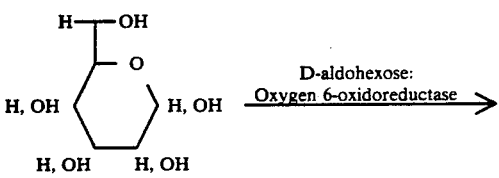

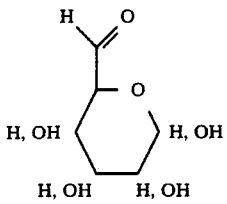

One example of a D-aldohexose:oxygen 6-oxidoreductase is galactose oxidase.

The term "catalase", as used herein, refers to $H_2O_2$:-$H_2O_2$ oxidoreductase which is identified as E.C. 1.11.1.6. Catalase is an oxidizing enzyme which decomposes hydrogen peroxide. These enzymes occur in both plane and animal cells. One example of a catalase which is effective in the present invention is the thymol-free bovine liver catalase distributed by Sigma Chemical Co. as Product Number C-40.

The term "sterile", as used herein, means free of living microorganisms.

All "percents" or "ratios" herein are on a weight basis unless otherwise specified. All values reported as a "molar equivalents" refer to the molar equivalents compared to a D-aldohexose-based starting material.

The method of converting a D-aldohexose-based compound to a derivative of a 5-hydroxymethyl-D-aldohexose-based compound is accomplished by employing the following steps.

1. Enzymic Oxidation of D-aldohexose-based Compound with D-aldohexose:oxygen 6-oxidoreductase The reaction is conducted in a clean vessel under agitation. A mixer with a tip speed of about 100–400 feet/min is preferred as an agitator. Sterile conditions are also preferred to prevent enzyme deactivation by microbial contamination.

An aqueous solution having a concentration of from about 1% to about 50%, preferably from about 10% to about 20% of D-aldohexose-based compound is prepared. The pH of the solution is adjusted to enhance reaction kinetics. A solution pH of from about 6 to about 8 is desired when using galactose oxidase as the enzyme. The desired pH may be achieved, for example, by buffering the solution or by simple titration. The solution temperature should be selected so as to minimize enzyme degradation.

Galactose oxidase enzymic conversion requires a temperature of from about 1° C. to about 50° C. The reaction can be run at temperatures up to the inactivation temperature of the enzyme. However, at higher temperatures microbial growth can be an issue. A temperature of from about 3° C. to about 25° C. provides good enzyme stability, good oxygen saturation values at standard pressure, and reasonable reaction kinetics for galactose oxidase, and is therefore particularly preferred. Preferably the reaction is run at 3° C. to 6° C. Typical reaction times are in the range of from about 1 to about 24 hours.

The purity of D-aldohexose:oxygen 6-oxidoreductase significantly influences its effectiveness as an oxidizing enzyme. These enzymes are traditionally reported in the art in terms of their unit activity per mg of protein (See Tressel et al., *Methods in Enzymology*, vol. 89, Pg. 167 (1982), and Bradford *Analytical Biochemistry*, 72, pp. 248-252 (1976)). This number can be readily be converted to unit activity per mole of 5-C-hydroxymethylaldohexose-based based compound. From about 1,000 to about 1,000,000 unit activity of enzyme per mole of D-aldohexose or D-aldohexose based compound is typically added to the solution. Preferably from about 100,000 to 300,000 unit activity is used.

The level of available oxygen in solution also affects the oxidation step. A saturated oxygen solution is preferred. Air and/or oxygen may be continuously bubbled through the solution to maintain oxygen saturation. This oxygenation is typically achieved by continuously pumping 2 to 3 volumes of air per volume of solution per minute using sparge rings having a high contact area. Other methods of increasing the availability of oxygen include reduced temperature operation (e.g., from about 3° C. to about 6° C.) operation under elevated pressure, and high speed mixing operation (100 feet/min. (about 30 m/min.) to about 400 feet/min. (120 m/min/) tip speed) with anti-foaming agents.

Suitable anti-foam agents include dimethyl silicone and other organosilicone compounds. FG-10 silicone from Dow Chemical works well in this process. The level of anti-foaming agent is from 10 to 100 ppm.

It is also advantageous to reduce or eliminate the amount of free peroxide in the reaction vessel. This is typically accomplished by adding to the solution from about 10,000 to about 2,000,000 unit activity of catalase per mole of D-aldohexose-based compound. However, other procedures for the removal of peroxide may be employed (e.g., precipitation and adsorption). It is preferred to immobilize the catalase when it is used or to recover and recycle it from aqueous solutions using ultrafiltration.

The presence of copper cations in the oxidation solution has been found to enhance enzyme stability. By maintaining from about 0.1 mM to about 2 mM of $CuSO_4$ in solution, enzyme stability is enhanced. Serum albumin is also a good enzyme stabilizer (See Kwiatkoski et al., *Biochemical and Biophysical Research Communications*, Vol. 53, No. 3 (1973)). Addition of these stabilizers are therefore preferred for optimal enzyme efficiency.

The addition of serum albumin at a level of about 0.6 g of protein per liter increases the reaction rate of the galactase oxidase oxidations. SBA is a serum albumin made by Armour Pharmaceutical Co., bovine albumin powder, Fraction V, Spec. No. 2293-01; it is preferred for use herein.

The preferred reaction utilizes galactose oxidase as the D-alsohexose:oxygen 6-oxidoreductase and a galactose-based starting material. Preferred galactose-based compounds include D-galactose (in all tautomeric forms), D-galactosyl polyols (e.g., lactitol), alkyl D-galactoside (e.g., ethyl galactoside), D-galactitol, D-galactonic acid, and di, tri-, oligo-, or polysaccharides comprising one or more of the above-mentioned simple sugar linkages (e.g., stachyose, raffinose, arabino-galactan). The most preferred reactions utilize about 10 to about 20% D-galactose-based compound solution, a pH from about 5 to about 8, a temperature from about 3° C. to about 6° C., from about 1000 to about 200,000 unit activity galactose oxidase/mole starting material, from about 10,000 to about 2,000,000 unit catalase activity/mole starting material, from about 0.1 mM to about 2mM $CuSO_4$, and a reaction time of from about 1 to about 24 hours. hours.

By way of example, the following conditions produce a 99% yield of methyl 5-C-hydroxymethyl-L-arabinohexopyranoside:
methyl ($\alpha$ or $\beta$)-D-galactoside starting material (about 15% in solution)
0.1 mM phosphate buffer, pH 7
Temperature = 4° C.
122,000 unit catalase activity per mole of starting material
86,500 unit galactose oxidase activity per mole starting material
Approximately 16 hour reaction time.

Finally, the catalase and D-aldohexose:oxygen 6-oxidoreductase are removed from the product solution. This can be done using conventional methods. The preferred separation technique is ultrafiltration through a membrane with from about 1,000 to about 30,000 molecular weight cut-off (MWCO). Ultrafiltration operations are described by Green, *Perry's Chemical Engineering Handbook*, 16th ed., ch. 17, pp. 27-34 (1984).

Immobilized enzymes are also preferred due to the fact that no subsequent enzyme removal step is required (See Masbach, *Methods in Enzymology*, Vols. 135 (1987), 136 (1987), 44 (1976)). The use of the triazine-coupling method (See Lily, *Methods in Enxymology*, Vol. 44, pg. 46 (1976) for the immobilization of galactose oxidase on polyethyleneimine silica (PEI-silica, J. T. Baker) produces effective immobilized enzyme.

2. Condensation of Oxidation Product With Formaldehyde to the 5-C-hydroxymethyl derivatives of D-galactose-based Compound From about 4 to about 40 molar equivalents of formaldehyde (most preferably from about 4 to about 8 molar equivalents) and from about 1 to about 13 molar equivalents of sodium hydroxide (most preferably from about 1 to about 3 molar equivalents) are added to the filtrate solution from step 1. A resulting concentration of from about 10% to about 30% substrate (i.e., the product from step 1. ) is preferred. A resulting pH between about 12 and about 13 is preferred. A pH of about 12.5 is most preferred. The reaction solution is maintained at a temperature of from about 15° C. to about 40° C. until completion of the reaction. Most preferably the temperature is maintained at from about 20° C. to about 25° C. Cooling may be required until the exothermic reaction has ceased (typically about 1 hour). The solution is agitated until the condensation reaction has achieved the desired degree of completion (about 1 to about 24 hours, typically 16 hours).

In order to control temperature and pH during the condensation reaction (thereby preventing aldehyde destruction) it is preferred to prereact the formaldehyde and sodium hydroxide in a separate operation. Typically, an aqueous formaldehyde solution and an aqueous sodium hydroxide solution are combined and agitated at from about 15° C. to about 35° C. until the exothermic reaction ceases (typically about 30 min.). The solution is then warmed to a temperature of from about 15° C. to about 40° C. and quickly added to the filtrate solution of step 1 while maintaining a temperature of from about 15° C. to about 40° C. The solution is agitated until the condensation reaction has achieved the desired degree of completion.

Other bases (e.g., $Ca(OH)_2$, KOH and mixtures of them) are also useful in the above-mentioned condensation reaction in place of all or part of the sodium hydroxide.

By way of example, under the following conditions about 75% yield of the 5-C-hydroxymethyl derivatives of D-galactose-based compounds are produced in about 24 hours using the above-described condensation reaction:

4:3:1 molar ratio of $CH_2O$/NaOH/galactose-based substrate

Temperature =25° C.

Another method of conducting the condensation reaction with formaldehyde is through the reaction of the sugar aldehyde which is produced via the galactose oxidase oxidation reaction and formaldehyde on a strongly basic resin. The oxidation product and the formaldehyde are contacted with a resin which has a pH of at least 11.5 at a temperature of from about 20 C. to about 50° C. for from 0.5 to 24 hours. A ratio of formaldehyde to sugar aldehyde of 4:1 to 8:1 is used. Preferably the ratio ia about 4:1 to about 5:1. The resin can have various levels of cross linking, ranging from about 2% to about 8%. Any commercial resin which is strongly basic can be used. Resin usage levels range from stoichiometric amounts (2.9 Meq) to an excess (30 Meq). The amount of resin will control the reaction kinetics of the condensation.

Sufficient salts and buffers are present in the oxidation reaction mixture to form and to maintain the highly basic conditions necessary to conduct the condensation reaction. As the reaction progresses, additional salts are generated from the formic acid formed and these are adsorbed by the resins. Methanol-free formaldehyde and cupric oxide as a catalyst, facilitate the reaction.

Formaldehyde condenses with itself to from "formose" sugar compounds which are adsorbed onto the resin. Since this condensation reaction is autocatalytic in nature, this adsorbtion slows the condensation reaction.

The resin condensation reaction simplifies the steps to make the intermediates of the 5-C-hydroxymethylhexoses. It also provides a purer compound, i.e. one which is free of formose compounds, and one which has a lower ash or salt content.

The yields from this reaction are greater, usually 10-15% higher than when other bases are used.

The product of this can be purified using fractional distillation to remove the excess formaldehyde and/or adsorption techniques in a manner similar to the other condensation reaction.

3. Purification

Unwanted ions (e.g., $Na^+$, $OH^-$, $H^+$) and residual formaldehyde should be removed from the resulting reaction solution. Purification can be accomplished by conventional means, such as by utilizing adsorption resins, dialysis, precipitation, or a combination of several techniques. The preferred method of deionization is to neutralize with acid, filter, then use an ion exchange resin absorption columns specific to the cations and anions which dissociate during step 2. The preferred method of removing low levels of unreacted formaldehyde is by utilizing an adsorption column specific to $CH_2O$. Steam stripping or vacuum flashing of formaldehyde may also be utilized. Fractional distillation can also be use to effectively remove the formaldehyde.

Particularly effective deionizing resins include Amberlite IR-120 ($H^+$) and IRA-400 ($OH^-$), manufactured by Rohm & Haas; a particularly effective formaldehyde specific resin is IRA-400 which has been converted from $OH^-$ion form via sodium bisulfite washing followed by a water washing. These resins are preferred. The preferred ($OH^-$) adsorption column operating temperature is about 50° C. Certain ions can be precipitated out. For example, where $Ca(OH)_2$ is used in step 2 above, saturation of the solution with carbon dioxide will precipitate out the calcium salt, which can easily be removed by filtration or centrifugation. Many salts may be precipitated via addition of strong mineral or organic acids (e.g. sulfuric acid or oxalic acid).

By way of example, the following purification parameters yield an essentially salt free (ash content <0.1%) and $CH_2O$-free solution ($CH_2O$ < 10 ppm) using adsorption resins at a temperature of about 50° C.:

1.9 meq/ml $H^+$ column absorption capacity 1.4 meq/ml $OH^-$ column absorption capacity 1.4 meq/ml $HSO_3^-$ column absorption capacity 4 bed volumes of 50° C. water to elute product from column.

4. Dewatering

The resulting solution from the above-mentioned purification step will generally contain from about 1% to 50% 5-C-hydroxymethylized product. In certain applications, the aqueous product solution which results from the above-mentioned purification step may be used directly. However, it is often advantageous to concentrate the product to higher levels (e.g., from about 90% to about 95% sugar).

Many of the 5-C-hydroxymethylated products are unstable and subject to decomposition (e.g., carmeling) at elevated temperatures. As a result, thermal evaporation may only be used on the dewatering unit operation where the product compound is sufficiently stable under the evaporation condition.

The preferred dewatering unit operation is reverse osmosis using conventional techniques described in Green, *Perry's Chemical Engineer's Handbook*, 6th ed, ch. 17, pp. 22-27 (1984).

It is desirable to concentrate the solution at low temperatures to prevent thermal breakdown of the 5-C-hydroxymethylated compound. Reverse osmosis employing a membrane with about a 100 MWCO (Molecular Weight Cut Off) and a 99% Nacl rejection at from about 10° C. to about 38° C. is preferred. Examples of these membranes include HR-98 or HR-99 polysulfone/polyamide thin film composite membranes, manufactured by Niro Corporation.

5A Hydrolysis

An optional processing step involves hydrolyzing 5-C-hydroxymethyl derivatives of D-galactose-based compounds produced by the above-described reaction to form bicyclic anhydro sugars. An example of this step is:

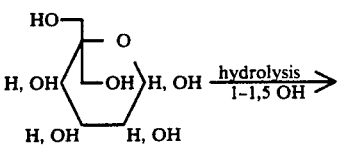

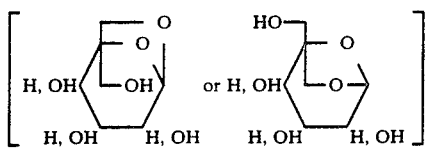

It has been found that these anhydro derivatives exhibit enhanced thermal stability without a loss of functionality when compared with their non-hydrolyzed counterparts (See U.S. patent application Ser. No. 190,485, Mazur, filed May 5, 1988.

The hydrolysis reaction is conducted by combining the 5-C-hydroxymethyl-D-aldohexose-based and a strong mineral acid or strong organic acid selected from the group consisting of sulfuric, hydrochloric, nitric, perchloric, and phosphoric acids, trifluoromethanesulfonic acid, methanesulfonic acid, and mixtures thereof (preferably sulfuric acid), at a molar ratio of from about 1:1 to about 1:10 (sugar:acid).

It is preferable to perform the reaction in an about 0.1 to about 1.0M aqueous solution, such as the one resulting from the purification step (step 3) above.

The reaction is conducted at a temperature of from about 20° C. to about boiling, preferably from about 80° C. to about 100° C.

By way of example under the following conditions an approximate yield of 70% of 1,6-anhydro-5-C-hydroxymethyl-D-aldohexose-based compound is achieved by:
Combine product solution from step 3 and concentrated sulfuric acid. Equimolar ratio of sulfuric acid and 5-C-hydroxymethyl-D-aldohexose-based compound.
Temperature = 100° C.
0.5-3 hour reaction time It should be noted that hydrolysis may also be carried out on a appropriate H+ column.

5B Removal of Residual Acid

Unwanted ions (e.g., H+, Cl−) should be removed from the product solution made by the hydrolysis reaction described in step 5A above. These ions can be removed by simple titration with a base (i.e., neutralization), whereby a food safe and/or easily removable salt is produced, or by adsorption techniques like the ones described in the purification step above.

The preferred deionization method is conventional adsorption using an OH− column like the one described in the purification step above.

By way of example the following neutralization parameters yield about 100% recovery of the anhydro-derivative and a final pH of about 7:
Temperature = 50° C.
4 bed volumes of 50-° C. water required to elute sugar from column 1.4 meq/ml resin absorptive capacity.

5C. Thermal Evaporation/Decolorization

The solution from step 5B may optionally be concentrated utilizing thermal evaporation and/or decolorized using activated carbon.

Decolorization is accomplished by contacting the solution resulting from step 5B with from about 5% to about 20% (sugar basis) activated carbon at room temperature. The carbon is removed by filtration.

The solution may be concentrated to about 90-95% with a short residence time evaporation (e.g., Luwa wiped film evaporator)

6. Crystallization

The most straightforward method of crystallizing the product 5-C-hydroxymethyl-aldohexose-based compound is by saturating an aqueous solution at an an elevated temperature and cooling it to precipitate out the product crystals. However, this technique can be hindered by impurities and by-products in the solutions. Impurities and by-products (to some degree) are detected in most synthesis. Since the primary utility for these compounds is in food compositions, it is essential to produce an unadulterated product. The following technique is the most effective for precipitating the product and reducing the level of impurities and by-products.

A 90-95% solution of the product compound is prepared as described in steps 4 or 5 above. The reaction product may be dried by removing water using ethanol (1:1) additions/evaporations (usually 1 or 2 such procedures are sufficient).

The solid residue resulting from the final ethanol evaporation is dissolved in methanol under reflux a ration of 1:1 to about 3:1 of methanol to solid is used. This is followed by the cooling of the solution to from about −10° C. to about 20° C., for from about 1 to about 12 hours.

The crystals are then filtered out and washed with cool methanol (about 0° C.).

Finally, residual methanol may be removed by drying and/or by recrystallization from water. The crystals can be washed with acetone to further remove impurities.

An efficient method for fractional crystallization of these compounds which provides an 80% to 85% yield requires that residuals glycosides, polyols and salts be removed from the syrup. The 5-C-hydroxymethylhexose compounds tend to form oils or "taffy like" precipitates. Hot methanol (approximately 50° C.) crystallization of the anhydrous syrup yields a greater than 95% pure compound. The heating of the oil or precipitate with a hot alcoholic solvent removes the residual glycosides, polyols, and free carbohydrates.

The use of hot alcohol solvent can eliminate either entirely or partially the need for salt removal from the starting syrup via the cationic/anionic deionization resin. Any food compatible alcoholic solvent can be used, as for example methanol or ethanol. The syrup must be dehydrated first. Water can be removed by using a food compatible solvent that azeotropically removes the water during distillation or by vacuum distillation. Free carbohydrate impurities (the starting material) can be removed by fermenting the feed syrup with bacteria or mold which utilize the carbohydrates but not the derivatives or compounds of this invention.

Preferably, the dehydrated or anhydrous syrup is incorporated into the alcoholic solvent using high sheer mixing and temperatures in excess of 50° C. Seeding with seed crystals speeds up the crystallization and can help to control the crystal particle size distribution. The agitation of the crystallization liquer promotes crystal growth rate. The amount of solvent and anhydrous syrup ratio will depend upon the particular novel compound. It is best to use the minimal amount necessary to dissolve the compound.

The crystallization solvents can be removed by vacuum, fluidized bed drying and other techniques known in the art.

The reactions described above can be adapted by one skilled in the art to utilize the following starting materials to produce their 5-hydroxymethyl derivatives:
D-aldohexoses
D-aldohexitols
D-aldohexosyl sugar alcohol saccharides (e.g. lactitol)
alkyl-aldohexosides (e.g. methyl D-galactoside, ethyl D-glucoside)
Di, tri-, oligo-, or polysaccharides containing at least one D-aldohexosyl group (e.g., stachyose, raffinose, arabinogalactan)
D-aldohexosyl-polyol compounds Furthermore, the batch processing steps described above can be adapted by one skilled in the chemical processing art to semi-bach, continuous or other processing schemes employing adequate recycle of recovered reagents to produce a commercially acceptable product.

The preparation of several of the foregoing compounds are fully described in the following examples.

EXAMPLE I

Preparation of methyl 5-C-hydroxymethyl-α-L-arabinohexopyranoside and 1,6-anhydro 5-C-hydroxymethyl-β-L-altropyranose from methyl β-D-galactopyranoside 1. Oxidation of Methyl β-D-Galactopyranoside (1) with Galactose Oxidase

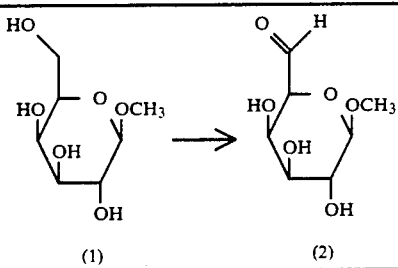

| | |
|---|---|
| methyl β-D-galactopyranoside (Sigma Chemical Co., No. M-6757) | 20.0 g |
| CuSO₄ | 66 mg |
| Phosphate Buffer, 100 mM, pH7 | 412.0 ml |
| Catalase, 16900 (Sigma Chemical Co., No. C-40) (approximately 1,231,000 unit activity/ mole starting material) | 126,750 unit activity |
| Galactose Oxidase (approximately 87,400 unit activity/mole starting material) | 9,000 unit activity |

The reaction is conducted in a one liter vessel equipped with an aerator and a propeller mixer. The mixer is run at a tip speed of 450 rpm. The reaction is run at 4° C. to minimize deactivation of galactose oxidase.

Methyl β-D-galactopyranoside (1) is dissolved in the aerated phosphate buffer containing the dissolved CuSO₄. The volume flow of air discharged by the aerator is regulated to produce an oxygen saturated solution while preventing severe foaming of the solution. A temperature of about 4° C. is maintained. The galactose oxidase and catalase are added and this solution is aerated for 20 hours.

The enzymes are removed from the product solution by ultrafiltration using a 10,000 MWCO membrane (Diaflo 13242, manufactured by Amicon). The resulting filtrate contains the oxidation product methyl β-D-galacto-hexodialdo-1,5-pyranoside (2).

2. Condensation of Oxidation Product With Formaldehyde to form Methyl 5-C-Hydroxymethyl-α-L-arabino-hexopyranoside

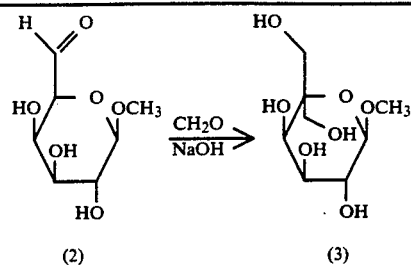

| Reagents | Amount |
|---|---|
| filtrate solution containing the oxidation product methyl β-D-galacto-hexodialdo-1,5-pyranose from step 1 | 400 ml |
| 37% formaldehyde solution (aqueous) (methanol stabilized) | 400 ml |
| 50% sodium hydroxide solution (aqueous) | 144 ml |

The sodium hydroxide solution and the formaldehyde solution are combined in a one liter vessel. The solutions are agitated for 30 minutes at about 10° C. The solution is warmed to about 25° C. and quickly added to the filtrate solution of step 1. A temperature of about 25° C. is maintained and a pH of 12.5 is maintained for about 24 hours. The reaction mixture is heated to 55° C. and deionized using ion exchange columns: first Amberlite IR-120(H+), then Amberlite IRA-400(OH−), both packings manufactured by Rohm & Haas. Finally, the deionized solution of the product is eluted through an Amberlite IRA-400 (HSO₃−) ion exchange column to remove the remaining formaldhyde. The column is packed with IRA-400 from Rohm & Haas, which has been treated by washing with sodium bisulfite (NaHSO₃) followed by water rinsing. Slow evaporation of the eluant at room temperature to dryness, followed by drying of the residue at room temperature under vacuum overnight produces 18.5 g (80%) of (3).

3. Preparation of 1,6-anhydro-5-C-hydroxymethyl-β-L-altropyranose

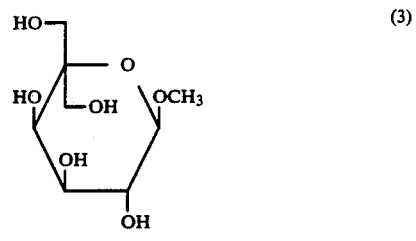

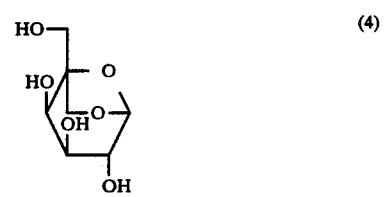

Methyl 5-C-hydroxymethyl-α-L-arabino-hexopyranoside (3) (59.0 g, 0.263 moles) is dissolved in 0.70M sulfuric acid (260 ml), and stirred at 100° C. for 90 minutes. The solution is cooled to room temperature and neutralized using an ion exchange resin (Amberlite IRA-400 (OH−), 250 ml). The filtrate is removed from the resin, and the filtrate is refluxed for 15 minutes with activated carbon (4.0 g). Carbon is removed with a glass fiber filter, and the filtrate is evaporated to dryness with ethanol. The white waxy residue is refluxed for 15 minutes with methanol (50 ml). The solution is stored overnight at 0° C. The product crystal are filtered to yield 20.0 g (39.6%) of 5-C-hydroxymethyl 1,6-anhydro-β-L-altropyranose (4). M.P.=166.5° C.-168.5° C. $[\alpha]_D^{23}=+145.1$ (7.2 c. in water)

EXAMPLE II

5-C-hydroxymethylation of lactitol.

1. Enzymic Oxidation of Lactitol

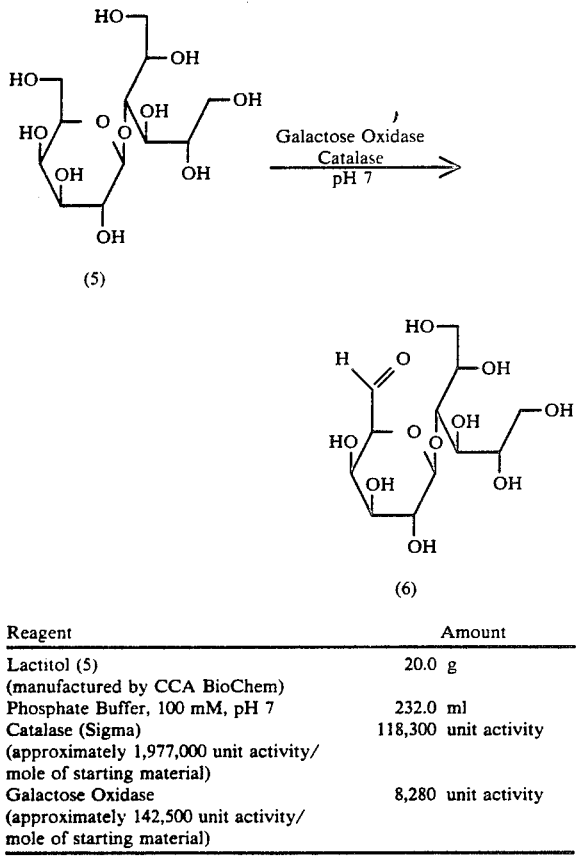

| Reagent | Amount |
| --- | --- |
| Lactitol (5) (manufactured by CCA BioChem) | 20.0 g |
| Phosphate Buffer, 100 mM, pH 7 | 232.0 ml |
| Catalase (Sigma) (approximately 1,977,000 unit activity/ mole of starting material) | 118,300 unit activity |
| Galactose Oxidase (approximately 142,500 unit activity/ mole of starting material) | 8,280 unit activity |

The reaction is conducted in a vessel equipped with a gentle aerator and a propeller mixer. The mixer is run at a tip speed of 450 rpm. The reaction is run at 4° C. to minimize deactivation of galactose oxidase.

Lactitol (5) is dissolved in the aerated phosphate buffer. At 4° C., the galactose oxidase and catalase are added and this solution is aerated to maintain oxygen saturation for 20 hours.

The enzymes are removed from the product solution by ultrafiltration using a 10,000 MWCO membrane (Diaflo 13242, manufactured by Amicon). The resulting filtrate contains the oxidation product (6).

2. Condensation of Oxidation Product With Formaldehyde

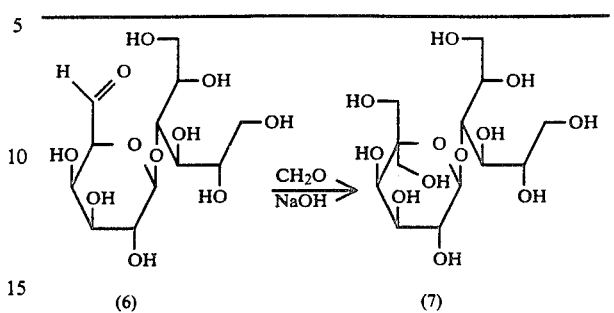

| Reagents | Amount |
| --- | --- |
| filtrate solution containing the oxidation product (6) from step 1 | 400 ml |
| 37% formaldehyde solution (aqueous, methanol stabilized) | 400 ml |
| 50% sodium hydroxide solution (aqueous) | 144 ml |

The filtrate solution and the formaldehyde solution are combined in a one liter vessel. The sodium hydroxide solution is added to the filtrate/formaldehyde solution over a period of 1 hour while the solution temperature is maintained between 20° C. and 25° C. with an ice-water bath. After the exothermic reaction has ceased, the ice-water bath is removed and the reaction mixture is stirred at room temperature for 16 hours. The reaction mixture is heated to 55° C. and deionized using ion exchanger columns: first Amberlite IR-120 (H+), then Amberlite IRA-400 (OH−). Finally, the deionized solution of the product is eluted through a column of Amberlite IRA-400, treated with $HSO_3^-$, in order to remove remaining formaldehyde. Evaporation to dryness followed by drying of the residue at room temperature under vacuum overnight produces 11.9 g 55% yield) of 5-C-hydroxymethyl-α-L-arabino-hexopyranosyl-D-glucitol (7).

A similar reaction may be run where the starting compound is, for example, raffinose (i.e., O-α-D-galactopyranosyl-(1→6)- α-D-glucopyranosyl-β-D-fructofuranoside), stachyose (i.e., O-α-D-galactopyranosyl-(1→6)-Oα-D-galactopryanosyl-(1→6)-α-D-glucopyranosyl-β-D-fructofuranoside), arabinogalactan, or D-galactopyranosyl glycerols.

The 5-C-hydroxymethylation of aldohexosyl groups described in Examples I and II, above, is readily adapted by one skilled in the art to other di-, tri and oligosaccharides containing at least one D-aldohexosyl or D-aldohexoside group (e.g., raffinose, stachyose and arabinogalactan).

What is claimed is:

1. A method of preparing 5-C-hydroxymethyl derivatives of D-galactose based compounds comprising the steps of:
    (a) reacting under agitation an aqueous solution comprising:
        (i) from about 1% to about 50% D-aldohexose-based compound or a mixture of D-aldohexose-based compounds, and
        (ii) from about 1,000 to about 1,000,000 unit activity of the enzyme D-aldohexose:oxygen 6-oxidoreductase per mole of D-aldohexose-based compound;

(b) reacting the solution produced by step (a) with from about 1 to about 40 molar equivalents of formaldehyde and from about 1 to about 13 molar equivalents of a base selected from the group consisting of sodium hydroxide, calcium hydroxide, and potassium hydroxide and mixtures thereof, at a temperature of from about 15° C. to about 40° C. and a pH of from about 12 to about 13; and (c) purifying the resulting aqueous 5-C-hydroxymethyl-D-aldohexose-based compound-containing solution.

2. A method according to claim 1 wherein said D-aldohexose:oxygen 6-oxidoreductase is galactose oxidase.

3. A method according to claim 2 wherein the reaction solution of step (a) further comprises from about 10,000 to about 2,000,000 unit activity of catalase per mole of D-aldohexose-based compound.

4. A method according to claim 3 wherein the enzyme used in step (a) is removed prior to step (b) by ultrafiltration using a membrane having a molecular weight cut off of from about 1,000 to about 30,000.

5. A method according to claim 3 wherein said galactose oxidase is immobilized.

6. A method according to claim 3 wherein the step (a) solution has a pH of from about 6 to about 8 and a temperature of from about 1° C. to about 50° C.

7. A method according to claim 6 wherein said reaction temperature of step (a) is from about 3+ C. to about 25° C.

8. A method according to claim 7 wherein the aqueous solution of step (a) comprises from about 10% to about 20% of a D-aldohexose-based compound which is a D-galactose based compound.

9. A method according to claim 8 wherein step (a) is conducted under sterile conditions.

10. A method according to claim 3 wherein step (a) is carried out in an oxygen saturated solution.

11. A method according to claim 3 wherein the reaction solution of step (a) further comprises from about 0.1 mM to about 2mM of copper cation.

12. A method according to claim 3 wherein the solution of step (a) further comprises form about 0.1 to about 1 g/L of serum albumin.

13. A method according to claim 10 wherein the mixture is mixed at a tip speed of 100 to 400 feet/minute (30 m/min. to 120 m/min.) and contacted with about 2 to about 3 volumes of air per volume of reactant.

14. A method according to claim 1 wherein, in step (b), the formaldehyde and the base are prereacted at a temperature of from about 0° C. to about 35° C. prior to combination with the solution produced by step (a).

15. A method according to claim 14 further comprising the step of dewatering the purified 5-C-hydroxymethylaldohexose-based compound-containing solution resulting from step (c).

16. A method according to claim 15 further comprising the step of crystallizing the 5-C-hydroxymethylaldohexose-based compound from the solution produced by step (c).

17. A method according to claim 14 wherein step (c) comprises:
(i) deionizing the solution using a process selected from the group consisting of adsorption, dialysis, precipitation, and combinations of two or more such processes; and
(ii) removing excess formaldehyde by adsorption or by fractional distillation followed by absorption.

18. A method according to claim 1 comprising the additional steps of:
(d) hydrolyzing the condensation product of step (c) with from about 1 to about 10 molar equivalents of an acid selected from the group consisting of sulfuric acid, nitric acid, hydrochloric acid, perchloric acid, phosphoric acid, methanesulfonic acid, trifluoromethane sulfonic acid, and mixtures thereof, wherein the temperature of the reaction mixture is maintained at from about 20° C. to about boiling; and
(e) removing any residual acid from the reaction mixture.

19. A method according to claim 18 wherein said reaction mixture temperature of step (d) is from about 80° C. to about 100° C.

20. A method according to claim 19, wherein in step (e), the residual acid is removed by neutralization followed by precipitation.

21. A method according to claim 19, wherein in step (e), the residual acid is removed by eluting the product solution of step (d) through an anion exchange column.

22. A method according to claim 19 further comprising the step of dewatering the solution resulting from step (e).

23. A method according to claim 3 wherein the enzyme is recovered and recycled.

24. A method according to claim 16 wherein the solvent is methanol and is used in a ratio of 1to 10.

25. A method of preparing 5-C-hydroxymethyl derivatives of D-galactose based compounds comprising the steps of:
(a) reacting under agitation an aqueous solution comprising:
(i) from about 1% to about 50% D-aldohexose-based compound or a mixture of D-aldohexose-based compounds, and
(ii) from about 1,000 to about 1,000,000 unit activity of the enzyme D-aldohexose:oxygen 6-oxidoreductase per mole of D-aldohexose-based compound;
(b) reacting the solution produced by step (a) with from about 1 to about 40 molar equivalents of formaldehyde in the presence of a resin containing hydroxide, ions at a pH of at least 11.5 and at a temperature of from about 20° C. to about 50° C. and
(c) purifying the resulting aqueous 5-C-hydroxymethyl-D-aldohexose-based compound-containing solution.

26. A method according to claim 25 wherein said D-aldohexose:oxygen 6-oxidoreductase is galactose oxidase.

27. A method according to claim 25 wherein the reaction solution of step (a) further comprises from about 10,000 to about 2,000,000 unit activity of catalase per mole of D-aldohexose-based compound.

28. A method according to claim 27 wherein the enzyme used in step (a) is removed prior to step (b) by ultrafiltration using a membrane having a molecular weight cut off of from about 1,000 to about 30,000.

29. A method according to claim 27 wherein said galactose oxidase is immobilized.

30. A method according to claim 27 wherein the step (a) solution has a pH of from about 6 and about 8 and a temperature of from about 1° C. to about 50° C.

31. A method according to claim 30 wherein said reaction temperature of step (a) is from about 3° C. to about 25° C. and wherein the aqueous solution of step (a) comprises from about 10% to about 20% of a D-aldohexose-based compound which is a D-galactose based compound.

32. A method according to claim 31 wherein step (a) is conducted under sterile conditions and further comprises from about 10,000 to about 2,000,000 unit activity of enzyme per mole of D-aldohexose-based compound.

33. A method according to claim 25 wherein step (a) is carried out in an oxygen saturated solution and further comprises from about 0.1 mM to about 2 mM of cupric sulfate.

34. A method according to claim 32 wherein, in step (b), the strongly basic resin usage levels range from stoichiometric amounts to an excess (2.9 Meq. to 30 Meq.).

35. A method according to claim 34 wherein the ratio of formaldehyde to oxidation product in step (b) is from about 4:1 to about 8:1.

36. A method according to claim 25 wherein the resin is from about 2% to about 8% crosslinked.

37. A method according to claim 16 wherein said compound is crystallized using an alcoholic solvent at a temperature of at least 50° C.

* * * * *